United States Patent [19]

Turkel et al.

[11] Patent Number: 5,792,074
[45] Date of Patent: Aug. 11, 1998

[54] PROTECTED MICROBIOLOGICAL SAMPLING BRUSH ASSEMBLY

[76] Inventors: David Turkel, 3319 Dominica Ct., Punta Gorda, Fla. 33950; Frank A. Scarfone, 3925 SW. 151st Ter., Miramar, Fla. 33027; Matthew S. Solar, 10520 Buenos Aires St., Cooper City, Fla. 33026; Herbert Cohen, 1091 Longview, Fort Lauderdale, Fla. 33326; David P. Gordon, 65 Woods End Rd., Stamford, Conn. 06905; Thomas A. Gallagher, 107 Barclay Dr., Stamford, Conn. 06903

[21] Appl. No.: 611,225

[22] Filed: Mar. 5, 1996

[51] Int. Cl.⁶ ............................................. A61B 5/00
[52] U.S. Cl. ............................................. 600/569
[58] Field of Search ........................... 128/750–754, 128/756, 759; 606/167, 170, 171, 205

[56] References Cited

U.S. PATENT DOCUMENTS

| | | | |
|---|---|---|---|
| 4,157,709 | 6/1979 | Schuster et al. | 128/759 |
| 4,586,604 | 5/1986 | Alter | 128/756 |
| 4,763,670 | 8/1988 | Manzo | 128/759 |
| 4,946,440 | 8/1990 | Hall | 128/756 |
| 5,129,402 | 7/1992 | Koll et al. | 128/759 |
| 5,318,589 | 6/1994 | Lichtman | 128/751 |
| 5,476,099 | 12/1995 | Robinson et al. | 128/751 |
| 5,490,861 | 2/1996 | Kratsch et al. | 128/751 |

FOREIGN PATENT DOCUMENTS

92014406  9/1992  WIPO ..................... 128/756

*Primary Examiner*—Max Hindenburg
*Attorney, Agent, or Firm*—David P. Gordon; David S. Jacobson; Thomas A. Gallagher

[57] ABSTRACT

A protected microbiological sampling brush assembly includes a sampling brush mounted on the distal end of a control wire, an inner catheter which houses the brush, an outer catheter which houses the inner catheter, and an elastomeric tip which is rigidly attached to the distal end of the outer catheter and which has a weakened end. The proximal ends of the control wire and catheters are coupled to a handle for independently moving the control wire, the inner catheter, and the outer catheter relative to each other. The weakened end of the elastomeric tip is preferably a slit which defines lips which are parted when the distal end of the inner catheter is moved distally against the elastomeric tip to allow the inner catheter to pass therethrough. When the inner catheter is moved proximally relative to the outer catheter, the lips of the elastomeric tip close to protect the inner catheter (and the sampling brush) from contamination. Easy to use handles which are attached to the proximal ends of the control wire, the inner catheter, and the outer catheter are disclosed.

18 Claims, 6 Drawing Sheets

PROTECTED MICROBIOLOGICAL SAMPLING BRUSH ASSEMBLY

This application is related to co-owned Ser. No. 08/275,291, filed Jul. 19, 1994, the complete disclosure of which is incorporated herein by reference.

BACKGROUND OF THE INVENTION

1. Field of the Invention

The present invention relates to an apparatus for obtaining microbiological specimens. More particularly, the invention relates to a microbiological (cytological) sampling brush which is protected from contamination during delivery to and removal from the specimen sampling site.

2. State of the Art

In order to assist in the diagnosis of various illnesses, it is often advisable to obtain a microbiological sample from a particular site within the human body. The microbiological sample is often obtained with a brush which is used to scrape the sampling site and thereby obtain a sample of the microorganisms present at the sampling site.

Several situations exist where it is necessary to obtain a microbiological sample of a local area within the body, but where access to the area cannot be gained without contaminating the sampling brush and/or the obtained sample. One such situation is in the case of ventilator-associated pneumonia. Ventilator-associated pneumonia (VAP) refers to an infection of the lower airways developing in patients with acute respiratory failure on mechanical ventilation. VAP is a significant contributor to mortality. Recent data indicate that appropriate antibiotic treatment of VAP significantly improves the outcome of VAP. Although appropriate antibiotics can improve the outcome of VAP, indiscriminate use of antibiotics facilitates colonization and superinfection with highly virulent pathogens. Therefore, it is important that antibiotics treatment be directed by the findings of quantitative cultures of lower respiratory secretions.

The clinical hallmarks of bacterial pneumonia include: fever, leukocytosis, production of purulent sputum, and a new or progressive density seen on a chest radiograph. Patients on mechanical ventilation, however, frequently have other conditions that cause fever and pulmonary densities. Therefore, it is impossible to make an accurate diagnosis on the basis of a chest radiograph and temperature reading alone. Sputum analysis is generally not possible due to the induced paralysis or neurological dysfunction of the patient's condition. Bronchoscopy provides access to the lower airways (bronchial tree) for visual inspection and sampling of secretions in the area of abnormality shown in the chest radiograph. With a bronchoscope in place, a catheter may be snaked through a lumen of the bronchoscope to obtain a sample from the area of abnormality. However, in order to reach the bronchial tree, the bronchoscope must traverse the endotracheal tube and the trachea. Purulent tracheal secretions are invariably present in most patients on prolonged mechanical ventilation. Secretions originate from the sinuses, the stomach, or the oropharynx and accumulate above the endotracheal cuff before being aspirated. These secretions contaminate the lumen of the bronchoscope as it traverses the endotracheal tube and the trachea and make it difficult or impossible to obtain an uncontaminated sample.

U.S. Pat. No. 4,235,244 to Abele et al. discloses a device having a microbiological brush which is protected from contamination during delivery of the brush to the sampling site. The brush is mounted on the distal end of a control wire which is housed within the lumen of a first inner catheter. The inner catheter is housed within the lumen of a second outer catheter or sheath and a non-toxic water-soluble waxlike plug seals the distal end of the second outer catheter. The proximal ends of the control wire, the inner catheter, and the outer catheter are coupled to a handle having three sliding components for independently moving the control wire, the inner catheter, and the outer catheter relative to each other. The distal plug prevents contaminants from entering the device and contaminating the brush as the device transits the lumen of the bronchoscope. When the distal end of the outer catheter is close to the sampling site, the inner catheter is moved distally relative to the outer catheter and the wax plug is expelled into the lung for eventual dissolution. The heretofore protected brush is then moved distally relative to the inner and outer catheters by movement of the control wire, and a sample is obtained. After the sample is obtained, the brush is moved proximally into the inner catheter and the brush and the inner catheter are both moved proximally into the outer catheter prior to withdrawal of the device from the bronchoscope. While the Abele et al. device is useful, it suffers from various drawbacks. For example, while the microbiological sampling brush is protected during delivery to the sampling site, it is not completely protected during withdrawal from the sampling site. Indeed, since the wax plug is not recovered, the distal ends of the catheters are no longer protected from contamination. Moreover, while the expelled wax plug does eventually dissolve, it can become a nidus for further infection prior to dissolution. In addition, while the three part handle of the Abele et al. device is operative to move the catheters and control wire relative to each other, it is difficult to operate and requires the use of both hands.

SUMMARY OF THE INVENTION

It is therefore an object of the invention to provide a microbiological sampling brush which is protected from contamination as it transits the lumen of a bronchoscope during delivery to a sampling site.

It is also an object of the invention to provide a microbiological sampling brush which is protected from contamination as it transits the lumen of a bronchoscope during recovery from a sampling site.

It is another object of the invention to provide a microbiological sampling brush assembly which does not deposit any foreign material inside the human body.

It is a further object of the invention to provide a microbiological sampling brush assembly which is easy to use and can be operated with one hand.

In accord with these objects which will be discussed in detail below, the protected microbiological brush assembly of the present invention includes a sampling brush mounted on the distal end of a control wire, a first inner catheter having a lumen housing the sampling brush, a second outer catheter having a lumen housing the first catheter, and an elastomeric tip which is attached to the distal end of the outer catheter. The proximal ends of the control wire, the inner catheter, and the outer catheter are coupled to one or more handles for independently moving the control wire, the inner catheter, and the outer catheter relative to each other. The elastomeric tip is weakened at its distal end by providing a slit (which may be sealed if desired), or a notch. The weakened distal end effectively provides a distal valve which defines lips which are parted when the distal end of the inner catheter is moved distally against the elastomeric tip, thereby allowing the inner catheter to pass through the elastomeric tip. When the inner catheter is moved proximally relative to the outer catheter, the lips of the elastomeric tip close to protect the inner catheter (and the sampling brush) from contamination.

According to a preferred aspect of the invention, the elastomeric tip is formed from polyurethane and is rigidly attached to the outer surface of the outer catheter by fusing, bonding, or mechanical attachment. The inner surface of the elastomeric tip may be provided if desired with a boss or ramp just proximal of the slit end to facilitate the opening of the weakened end. According to another preferred aspect of the invention, an easy to use handle mechanism is attached to the proximal ends of the control wire, the inner catheter, and the outer catheter. A first embodiment of the handle mechanism includes a single lever which progressively engages the proximal ends of the inner catheter and the control wire so that when the lever is moved in a first direction, the inner catheter is moved through the elastomeric tip before the brush is moved distally out of the end of the inner catheter. Movement of the lever in the opposite direction draws the brush into the distal end of the inner catheter before moving the inner catheter back into the distal end of the outer catheter and closing the elastomeric tip. A second embodiment of the handle mechanism includes a trigger which is coupled to a rack member and to a pair of pinion gears which are progressively engaged by the rack member as the trigger is pulled. The proximal ends of the inner catheter and the control wire are provided with separate rack members which are each engaged by a respective one of the pinion gears.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
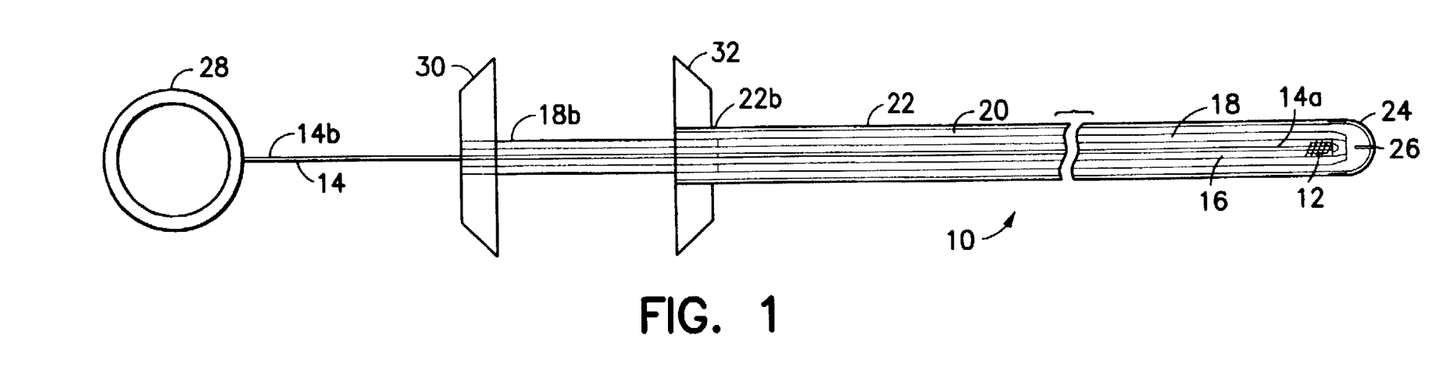
FIG. 1 is a broken schematic side elevation view in partial section of a first embodiment of the microbiology sampling brush assembly of the invention.
Figure 2:
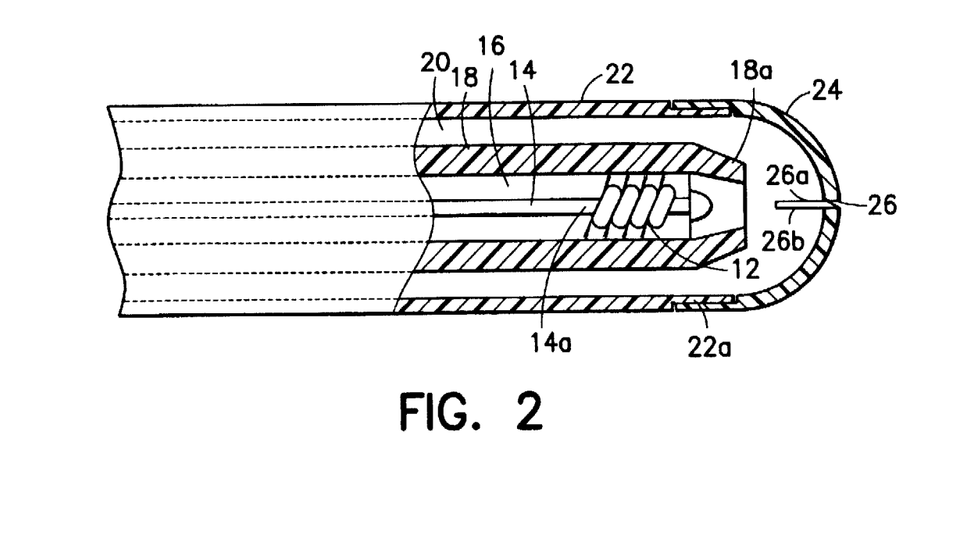
FIG. 2 is an enlarged broken side elevation view in partial section of the distal end of the brush assembly of FIG. 1 with the brush and inner catheter in a first position.
Figure 2A:
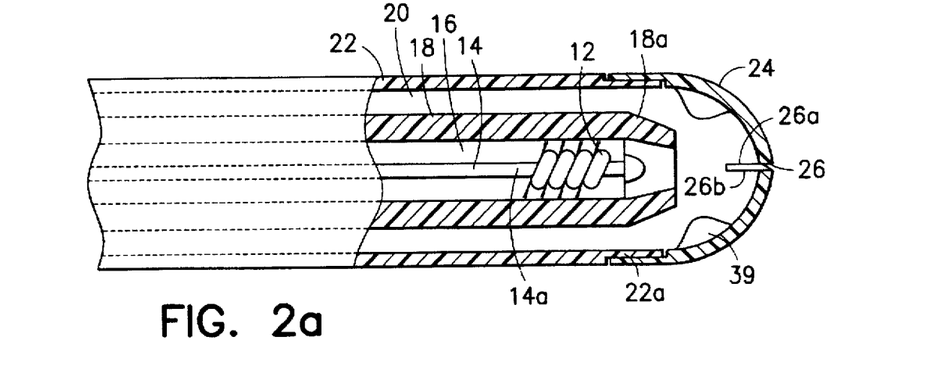
FIG. 2a is an enlarged broken side elevation view in partial section of an alternative distal end for the brush assembly of FIG. 1 with the brush and inner catheter in a first position.

Referring now to FIGS. 1 and 2, a protected microbiological brush assembly 10 according to the invention includes a sampling brush 12 mounted on the distal end 14a of a control wire 14, with the brush 12 and the wire 14 being housed within a lumen 16 of a first (inner) catheter 18, which in turn is housed within the lumen 20 of a second (outer) catheter 22. The distal end 22a of the outer catheter 22 is provided with an elastomeric tip 24 having a weakened distal end 26 (e.g., a slit). The proximal end 14b of the control wire 14 is coupled to a thumb ring 28, while the proximal ends 18b, 22b of the inner and outer catheters 18, 22 are coupled respectively to first and second finger grips 30, 32 which are located distally of the thumb ring 28. The proximal end 22b of the outer catheter 22 and the finger grip 32 are located distally of the first finger grip 30. From the foregoing, it will be appreciated that the control wire 14, the inner catheter 18, and the outer catheter 22 may be moved independently relative to each other by movement of the thumb ring 28 and the two finger grips 30, 32 relative to each other. It will further be appreciated that the distal slit 26 of the elastomeric tip 24 defines lips 26a, 26b through which the distal end 18a of the inner catheter 18 can be moved. To facilitate parting of the lips 26a, 26b, the distal end 18a of the inner catheter 18 is preferably tapered as seen best in FIG. 2. In addition, the elastomeric tip may be provided with a ramp or boss 39 adjacent the distal end as seen in FIG. 2a. The ramp or boss 39 may extend circumferentially around the inner surface of the elastomeric tip or more preferably may divided into two or more axially aligned ramps or bosses which are spaced around the circumference.

According to a presently preferred embodiment, the catheters 18 and 22 are preferably made of a slippery plastic material such as polyurethane, polyethylene, TEFLON, or polypropylene. The outer diameter of the outer catheter 22 is preferably approximately 1.8 millimeters and the overall length of the outer catheter is preferably approximately one meter. Those skilled in the art will appreciate that the inner catheter 18 is slightly longer than the outer catheter 22 and has a smaller outer diameter so that it can traverse the lumen of the outer catheter. It will also be understood that the control wire is longer than the inner catheter and that the outer diameter of the brush is smaller than the inner diameter of the inner catheter The elastomeric tip 24 is formed from polyurethane and is rigidly attached to the outer surface of the outer catheter by heating, solvent bonding, gluing or other means. As aforementioned, the distal end of the tip 24 is weakened to permit movement of the inner catheter therethrough. Accordingly, the tip 24 may have a slit (such as slit 26) which extends either partially through or completely through the thickness of the elastomer. If desired, the slit may be sealed such as by dipping a polyurethane tip in a solvent such as tetrahydrofuran (THF), or by applying a UV adhesive and curing the adhesive with UV light. Alternatively, a notch may be provided in the distal end of the tip to provide an area of reduced thickness.

Figure 3:
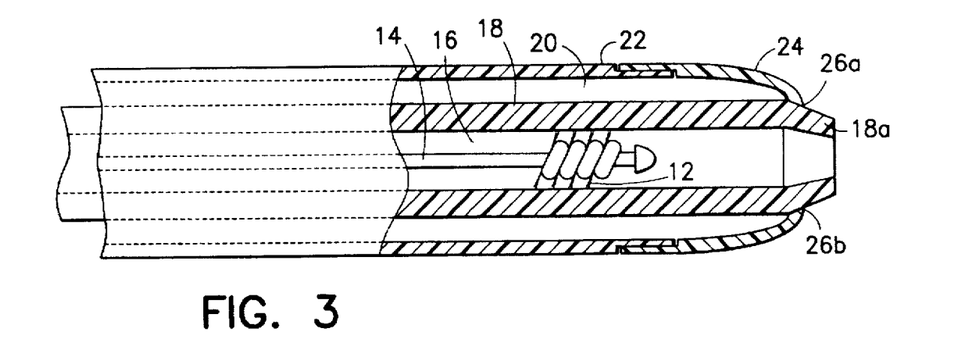
FIG. 3 is a view similar to FIG. 2 with the brush and inner catheter in a second position.
Figure 4:
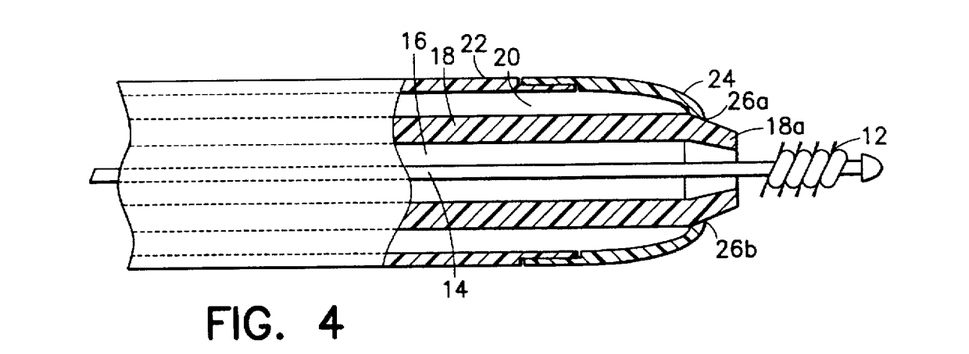
FIG. 4 is a view similar to FIGS. 2 and 3 with the brush and inner catheter in a third position.

Turning now to FIGS. 3 and 4, and with reference to FIG. 1, it will be appreciated that when the inner and outer finger grips 30, 32 are moved together, the distal end 18a of the inner catheter 18 and the elastomeric tip 24 attached to the outer catheter 22 are brought into contact and the lips 26a, 26b defined by the slit 26 are parted as shown in FIG. 3. This permits the distal end 18a of the first catheter 18 to pass through the elastomeric tip 24. It will also be appreciated that after the first and second catheters are moved to the respective positions shown in FIG. 3, movement of the thumb ring 28 towards the finger grips 30, 32 moves the sampling brush 12 out of the distal end 18a of the inner catheter 18 as shown in FIG. 4. In this position, the brush 12 is available to obtain a microbiological Referring now to FIGS. 1–4, the protected microbiology brush assembly is preferably used to obtain a microbiological sample in the following manner: With the catheters and the control wire in the relative positions substantially as shown in FIG. 1, the distal end of the outer catheter is advanced through the lumen of a bronchoscope (not shown) until it is close to the sampling site. Those skilled in the art will appreciate that during this procedure, the elastomeric tip prevents contaminants from entering the lumen of the outer catheter and thus from entering the lumen of the inner catheter and contaminating the sampling brush. When the distal end of the outer catheter is near the sampling site, the finger grips 30, 32 are moved together and the distal ends of the inner and outer catheters assume relative positions substantially as shown in FIG. 3. The thumb ring 28 is then moved distally so that the brush exits the distal end of the inner catheter as shown in FIG. 4. The brush is typically moved back and forth several times at the sampling site (not shown) and a sample is obtained. The thumb ring 28 is then moved proximally and the brush with the sample is withdrawn into the lumen of the inner catheter as shown in FIG. 3. The finger grips 30, 32 are moved apart and the catheters are brought back to the position shown in FIGS. 1 and 2. It will be appreciated that the elastomeric tip is now in a position to protect the lumen of the catheters and the sampling brush from contamination while the catheters are withdrawn from the bronchoscope. It will also be appreciated that no foreign material is left at the sampling site.

Turning now to FIGS. 5, 5a, 6, 7, and 8, a second embodiment of a protected microbiology sampling brush assembly 100 is substantially the same as the brush assembly 10 described above, except for the proximal actuator 102. In this second embodiment of the invention, the proximal actuator 102 includes a stationary handle 104 and a movable lever 106. The stationary handle 104 has a lower finger ring 108 and an upper stepped through bore 110. The stepped throughbore 110 has a larger diameter proximal portion 112 and a smaller diameter distal portion 114 with the smaller diameter distal portion 114 is coupled to the proximal end 22a of the outer catheter 22 (described above). The larger diameter portion 112 is provided with a lower slot opening 116. A first cylindrical rack member 118 having a throughbore 118a is slidably disposed in the larger diameter portion 112. The proximal end 18a of the inner catheter 18 (described above) is coupled to the first rack member 118. A second cylindrical rack member 120 is also slidably disposed in the larger diameter portion 112 and proximal of the first rack member 118. The control wire 14 passes through the throughbore 118a of the first rack member, and the proximal end 14a of the control wire 14 is coupled to the second rack member 120.

The movable lever 106 of the actuator 102 is provided with a lower thumb ring 122 and two upper pinion gears 124, 126. The movable lever 106 is coupled to the stationary handle 104 by a pivot axle 128 and is arranged so that the upper pinion gears 124, 126 may enter the larger diameter portion 112 of the throughbore 110 through the lower slot opening 116 in the proximal portion of the handle 104. The upper pinion gears 124, 126 are spaced apart from each other so that the distal pinion gear 124 engages the first rack member 118 and the proximal pinion gear 126 engages the second rack member 120 as described below. As shown in the Figures, the first rack member 118 has a plurality of cogs and the distal pinion gear 124 has a corresponding plurality of teeth, whereas, the second rack member 120 has only two cogs and the proximal pinion gear 126 has only one tooth. More significant, however, is the fact that the distal pinion gear teeth are shorter than the proximal pinion gear tooth. The tooth receiving spaces between the cogs of the two rack members are also different to accommodate the different sized teeth. From the following description, those skilled in the art will appreciate that the proximal pinion gear tooth 126 is taller than the distal pinion gear teeth 124 so that both rack members can be engaged by the respective pinion gears which pivot about a common axle 128.

Figure 5:
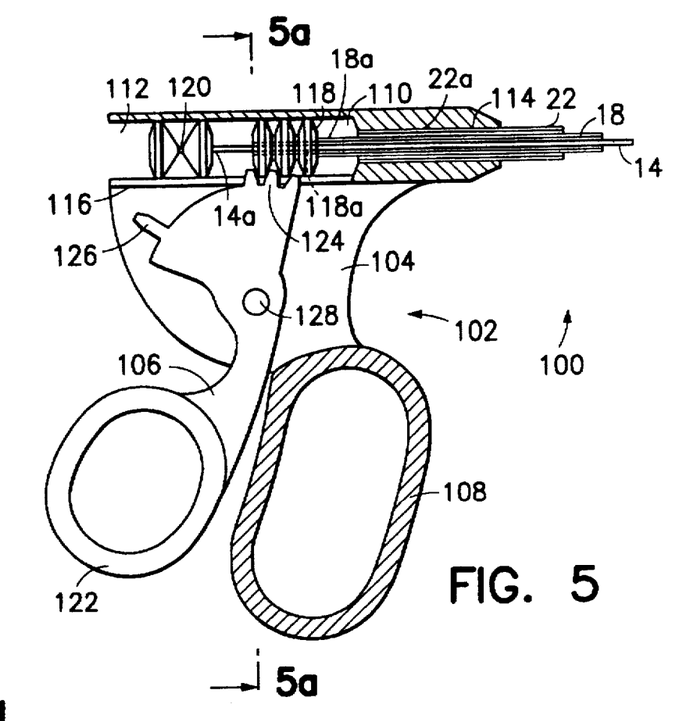
FIG. 5 is a broken side elevation view in partial section of a first embodiment of a preferred proximal handle of the invention in a first position.
Figure 5A:
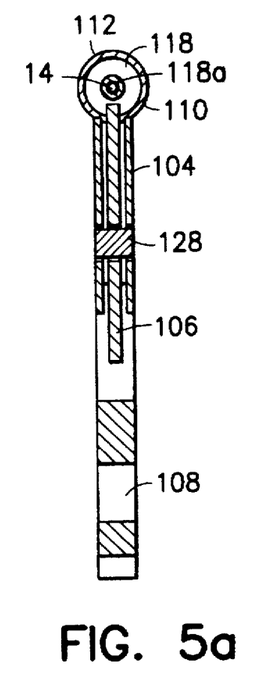
FIG. 5a is a section taken along the line 5a—5a in FIG. 5.
Figure 6:
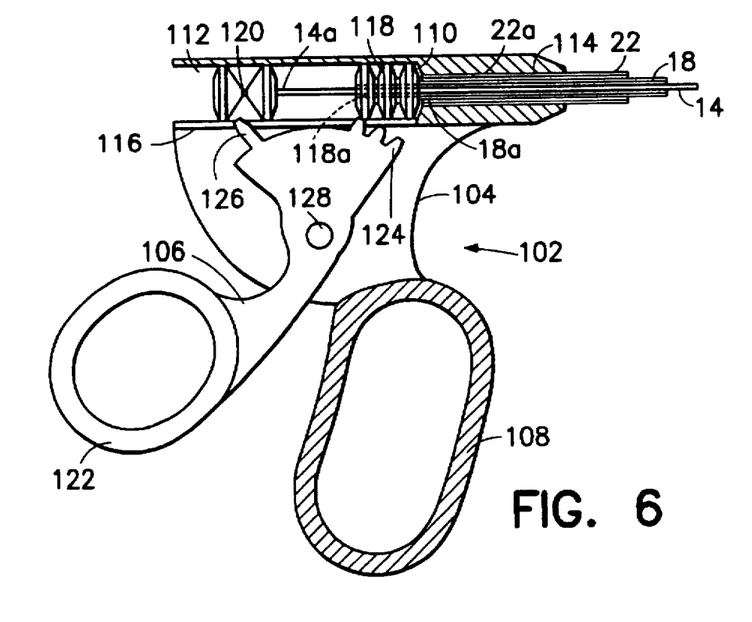
FIG. 6 is a view of the handle of FIG. 5 in a second position.
Figure 7:
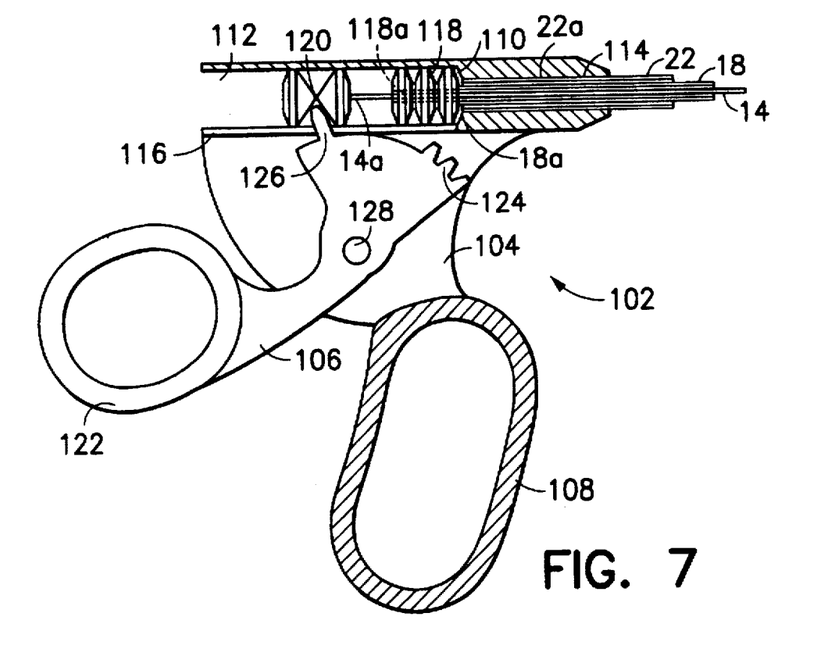
FIG. 7 is a view of the handle of FIGS. 5 and 6 in a third position.
Figure 8:
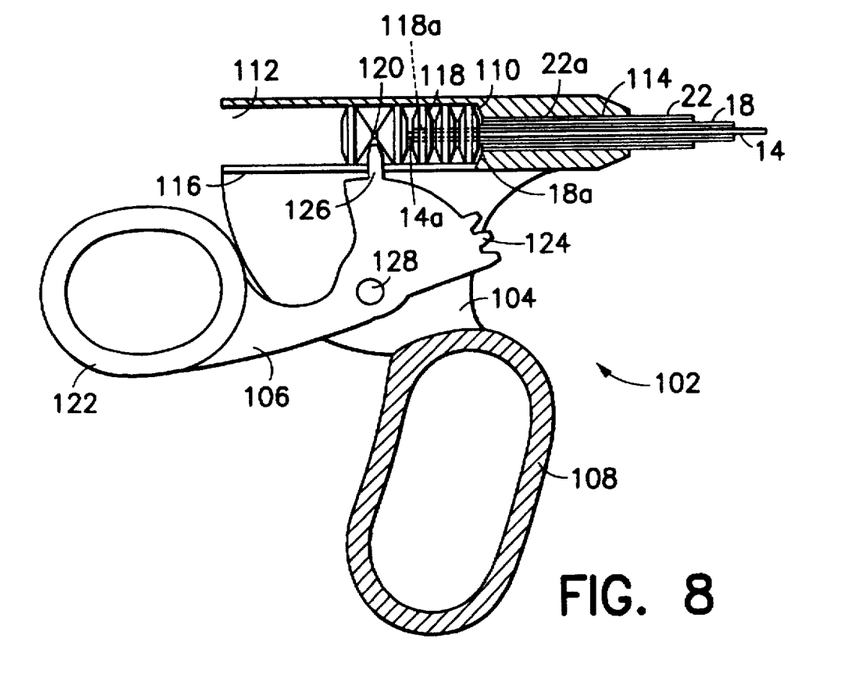
FIG. 8 is a view of the handle of FIGS. 5–7 in a fourth position.

The actuator mechanism 102 operates as follows. Starting from a first position shown in FIG. 5 in which the distal pinion gear 124 engages the first rack member 118, the movable lever 106 is rotated about the pivot axle 128 so that the thumb ring 122 is moved away from the finger ring 108 of the stationary handle 104. This rotation moves the first rack member 118 distally as shown in FIG. 6. It will be appreciated that when the first rack member 118 is moved distally, the inner catheter 18 is also moved distally relative to the outer catheter 22 and relative to the brush 12. As seen in FIG. 6, it will also be appreciated that after the distal pinion gear 124 disengages from the first rack member 118, the proximal pinion gear 126 comes into engagement with the second rack member 120. Further rotation of the lever 106 to the position shown in FIG. 7, e.g., moves the second rack member 120 distally which results in the control wire 14 being moved distally. Thus, when the actuator mechanism is in the position substantially as shown in FIG. 6, the distal ends of the catheters and the sampling brush are in the position substantially as shown in FIG. 3. Further rotation of the lever 106 to the position shown in FIG. 8 continues to advance the second rack member 120 without further advancing the first rack member 118 (i.e. without further advancing the inner catheter 18). Thus, when the actuator mechanism reaches the position substantially as shown in FIG. 8, the distal ends of the catheters and the sampling brush are in the position substantially as shown in FIG. 4. In this position, the thumb ring 122 may be rotated back and forth through a small arc to effect a back and forth movement of the brush for gathering a sample.

Rotation of the lever 106 in the opposite direction (i.e. so that the thumb ring 122 is moved toward the finger ring 108 of the stationary handle 104) causes the control wire 14 to be moved proximally, thereby withdrawing the sampling brush 12 back into the inner catheter 18 to the position substantially as shown in FIG. 3. Further rotation of the lever 106 in this direction causes the distal pinion gear 124 to engage the first rack member 118 and to thereby move the inner catheter 18 in the proximal direction back to the position substantially as shown in FIG. 5. When the actuator 102 is returned to the position substantially as shown in FIG. 5, the distal ends of the catheters and the sampling brush are returned to the positions substantially as shown in FIG. 2, and the lips 26a, 26b of the elastomeric tip are closed, thereby preventing contamination of the brush during withdrawal of the assembly.

From the foregoing, those skilled in the art will appreciate that the preferred movement of the inner catheter 18 and the control wire 14 relative to the outer catheter 22 and relative to each other is subject to some variation while still achieving the objects of the invention. According to the invention, it is necessary that the brush not be moved out of the inner catheter until after the inner catheter has passed through the elastomeric tip. It is also necessary that the inner catheter not be moved back within the elastomeric tip until the brush is first moved back within the inner catheter. Within those parameters, it is possible to move the brush and inner catheter simultaneously through the elastomeric tip and then move the brush distally through the inner catheter. Alternatively, the brush may be kept stationary while the inner catheter is moved through the elastomeric tip. Those skilled in the art will appreciate that there are many variations possible within these stated parameters.

Turning now to FIGS. 9–12, a third embodiment of a protected microbiology sampling brush assembly 200 is substantially the same as the brush assemblies 10 and 100 described above, except for the proximal actuator 202. In this third embodiment of the invention, the proximal actuator 202 includes a stationary handle 204 and a spring biased trigger 206. The stationary handle 204 has a lower finger or thumb ring 208 and an upper stepped through bore 210. The stepped throughbore 210 has a larger diameter proximal portion 212 and a smaller diameter distal portion 214 with the smaller diameter distal portion 214 is coupled to the proximal end 22a of the outer catheter 22 (described above). The larger diameter portion 212 is provided with a lower slot opening 216 and, optionally, a proximal cap 217. A first cylindrical rack member 218 having a throughbore 218a is slidably disposed in the larger diameter portion 212. The proximal end 18a of the inner catheter 18 (described above) is coupled to the first rack member 218. A second cylindrical rack member 220 is also slidably disposed in the larger diameter portion 212 and proximal of the first rack member 218. The control wire 14 passes through the throughbore 218a of the first rack member, and the proximal end 14a of the control wire 14 is coupled to the second rack member 220. A first rotatable pinion gear 222 is mounted below and engages the first rack member 218 and a second rotatable pinion gear 224 is mounted below and engages the second rack member 220. A rack guiding slot 226 is provided below the pinion gears for guiding the trigger 206 as described below. The upper distal end of the guiding slot 226 is provided with a stop 227.

Figure 9:
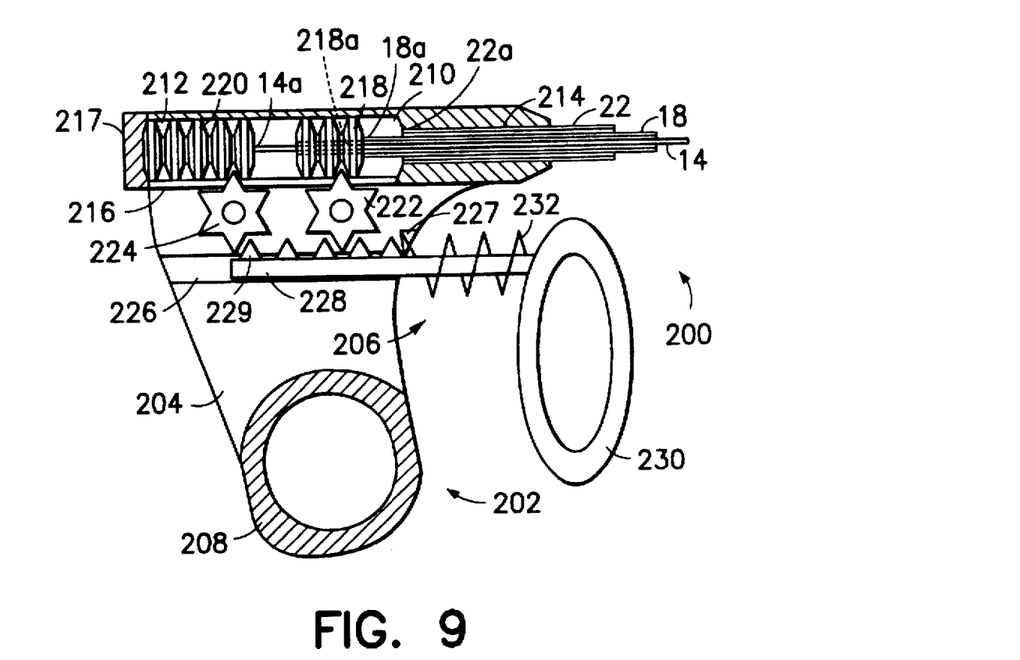
FIG. 9 is a broken side elevation view in partial section of a second embodiment of a preferred proximal handle of the invention in a first position.

The trigger 206 includes a trigger rack 228 having a plurality of teeth 229 and a finger ring 230 which is removably coupled to the distal end of the trigger rack 228. The trigger rack 228 is slidably mounted in the guiding slot 226 of the handle 204. The trigger 206 is preferably biased in the distal direction by a spring 232. The stop 227 in the handle 204 prevents the trigger rack 228 from exiting the distal end of the guiding slot 226. Those skilled in the art will appreciate that the trigger 206 may be mounted in the handle 204 by inserting the trigger rack 228 through the proximal end of the guiding slot 226 before attaching the finger ring 230 to the distal end of the trigger rack 228. After assembly, the actuator 202 assumes a configuration substantially as shown in FIG. 9. In this first position, the trigger rack 228 is biased distally against the stop 227 by the spring 232 and the cylindrical rack members 218, 220 are in relatively proximal positions. When the actuator 202 is in the position shown in FIG. 9, the distal end of the assembly 200 is in the position substantially as shown in FIG. 2.

Figure 10:
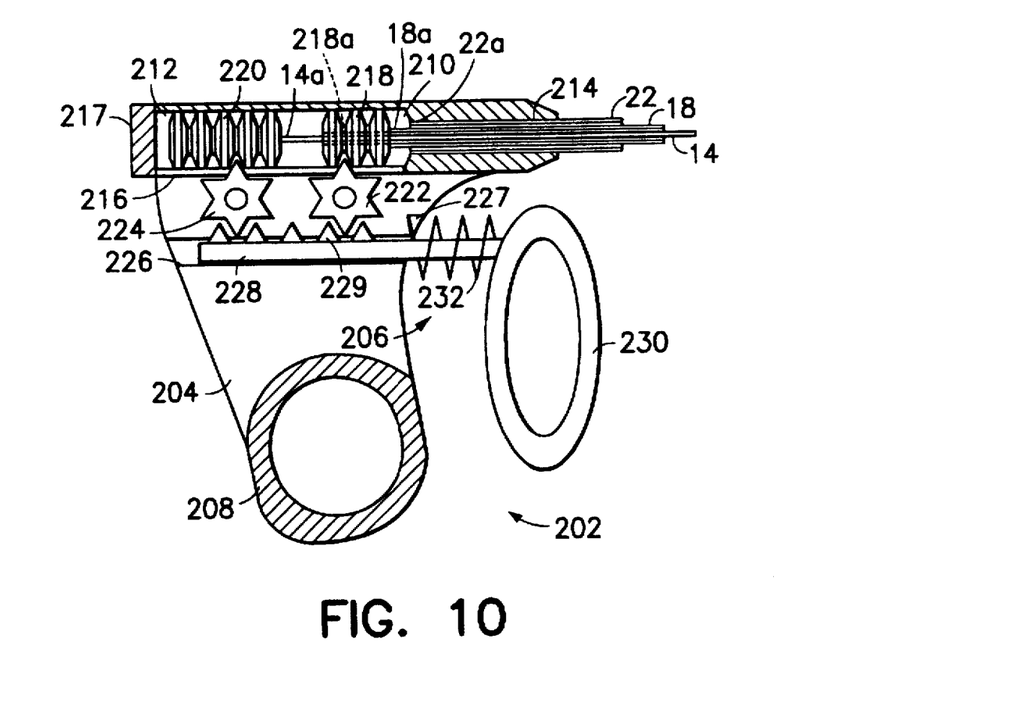
FIG. 10 is a view of the handle of FIG. 9 in a second position.

The actuator 202 operates as follows. As the trigger 206 is squeezed proximally against the spring 232, the trigger rack 228 engages both pinion gears 222, 224 and rotates them clockwise. The rotation of the pinion gears results in a distal translation of the cylindrical rack members 218, 220 as shown in FIG. 10. It will be appreciated that, as shown in FIGS. 9–12, the teeth 229 on the trigger rack 228 are arranged so that when the trigger is first squeezed both pinion gears are engaged and thus, both cylindrical rack members 218, 220 are moved distally. This results in both the inner catheter 18 (FIGS. 2–4) and the brush 12 being moved distally together. Further proximal movement of the trigger 206 to the position shown in FIG. 11 continues to move both the inner catheter and the brush together until the teeth 229 on the trigger rack 228 are all located proximal of the first pinion gear 222. When the trigger is in the position shown in FIG. 11, the inner catheter 18 is in the position substantially as shown in FIG. 3. Further proximal movement of the trigger 206 will no longer affect the position of the inner catheter since the teeth 229 are no longer in a position to engage the first pinion gear 222. It will also be appreciated that proximal slippage of the inner catheter is substantially prevented by frictional engagement of the lips 26a, 26b (FIG. 3) against the distal end of the catheter 18. When the trigger 206 is moved from the position shown in FIG. 11 to the position shown in FIG. 12, the brush 12 (FIGS. 2–4) is moved out of the catheter 18 to the position substantially as shown in FIG. 4.

Figure 11:
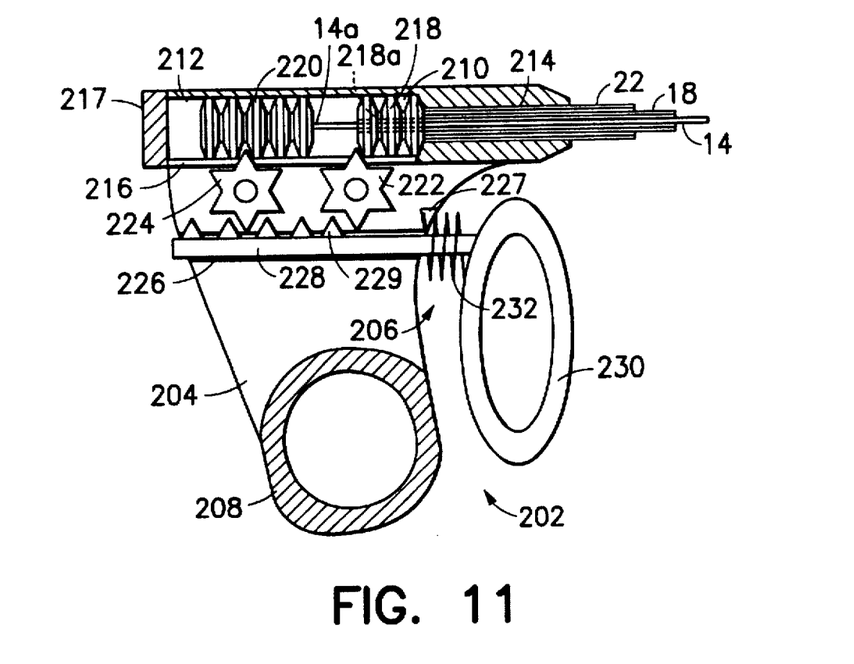
FIG. 11 is a view of the handle of FIGS. 9 and 10 in a third position.
Figure 12:
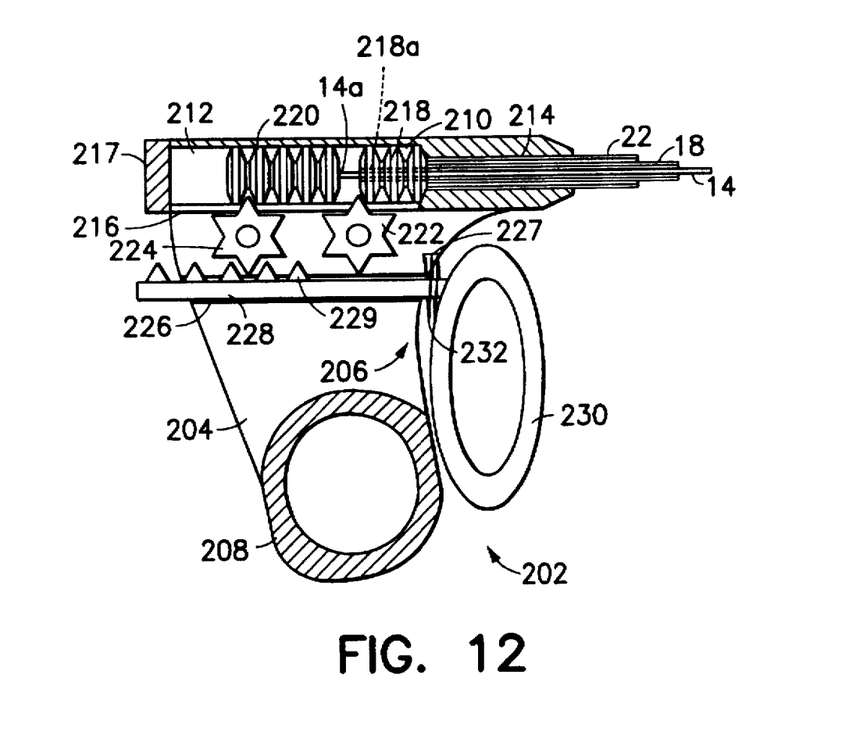
FIG. 12 is a view of the handle of FIGS. 9–11 in a fourth position.

Movement of the trigger 206 back and forth between the positions shown in FIGS. 12 and 11, effects a back and forth movement of the brush 12 which is effective for brushing tissue to obtain a good sample. After a sample is obtained, the practitioner need only release the trigger 206 and the spring 232 will move the trigger rack 228 distally, reversing the process described above. That is, the teeth 229 will first engage the second pinion gear 224 so as to move the brush 12 proximally into the catheter 18 before the teeth engage the first pinion gear 222 (FIG. 11) and begin to move both the catheter and the brush proximally to the position shown in FIG. 2, when the trigger is in the position shown in FIG. 9.

There have been described and illustrated herein several embodiments of a protected microbiology sampling brush assembly. While particular embodiments of the invention have been described, it is not intended that the invention be limited thereto, as it is intended that the invention be as broad in scope as the art will allow and that the specification be read likewise. Thus, while particular materials and dimensions have been disclosed, it will be appreciated that other materials and dimensions could be utilized. Also, while three different actuators have been shown, it will be recognized that other types of actuators could be used. Moreover, while particular actuator configurations have been disclosed in reference to rack and pinion couplings, it will be appreciated that other configurations could be used as well. Furthermore, while one of the actuators has been disclosed as having thumb ring lever which is movable relative to a finger ring handle, it will be understood that a finger ring lever which is movable relative to a thumb ring handle can achieve the same or similar function as disclosed herein. It will also be appreciated that the relative placement and dimensions of the disclosed racks and pinions may be varied while still obtaining substantially the same results as described herein. Additionally, as used herein, the term "catheter" should be construed broadly to mean virtually any open tube having a lumen.

Those skilled in the art will also appreciate that while several preferred automatic sealing means were described, including an elastomeric member having either a distal slit or a weakened or notched end, other automatic sealing means could be utilized. For example, a duck-billed valve, a slit valve, or other appropriate valves which would permit the inner catheter to extend through, and then automatically close upon withdrawal of the catheter could be used as the automatic sealing means. It will therefore be appreciated by those skilled in the art that yet other modifications could be made to the provided invention without deviating from its spirit and scope as so claimed.

We claim:

1. A protected microbiological sampling brush assembly, comprising:
   a) a control wire having a proximal end and a distal end;
   b) a sampling brush coupled to said distal end of said control wire;
   c) an inner catheter having a proximal end, a distal end having a tapered outer surface, and a lumen extending from said proximal end to said distal end, said control wire being disposed within said lumen of said inner catheter;
   d) an outer catheter having a proximal end, a distal end, and a lumen extending from said proximal end to said distal end, said inner catheter being disposed within said lumen of said outer catheter;
   e) automatic sealing means coupled to said distal end of said outer catheter for sealing access to said lumen of said outer catheter, said automatic sealing means comprising a substantially hemispherical elastomeric member provided with a sealed distal slit extending through said elastomeric member and an inside surface having a protrusion, said automatic sealing means being automatically opened by distal movement of said inner catheter relative to said outer catheter which causes said inner catheter to engage said protrusion prior to reaching said automatic sealing means, thereby expediting opening of said sealing means, and being automatically closed by proximal movement of said inner catheter relative to said outer catheter; and
   f) proximal actuation means coupled to said proximal ends of said control wire, said inner catheter, and said outer catheter for moving said inner catheter relative to said outer catheter such that said distal end of said inner catheter extends through said automatic sealing means, and for moving said control wire relative to said inner catheter such that said sampling brush extends past said distal end of said inner catheter.

2. An assembly according to claim 1, wherein:
   said elastomeric member is made of polyurethane.

3. An assembly according to claim 1, wherein:
   said proximal actuation means includes a thumb ring coupled to said proximal end of said control wire, a first finger grip coupled to said proximal end of said inner catheter, and a second finger grip coupled to said proximal end of said outer catheter.

4. A protected microbiological sampling brush assembly, comprising:
   a) a control wire having a proximal end and a distal end;
   b) a sampling brush coupled to said distal end of said control wire;
   c) an inner catheter having a proximal end, a distal end, and a lumen extending from said proximal end to said distal end, said control wire being disposed within said lumen of said inner catheter;
   d) an outer catheter having a proximal end, a distal end, and a lumen extending from said proximal end to said distal end, said inner catheter being disposed within said lumen of said outer catheter;
   e) automatic sealing means coupled to said distal end of said outer catheter for sealing access to said lumen of said outer catheter, said automatic sealing means comprising a substantially hemispherical elastomeric member having a weakened distal end, said automatic sealing means being automatically opened by distal movement of said inner catheter relative to said outer catheter and being automatically closed by proximal movement of said inner catheter relative to said outer catheter; and
   f) proximal actuation means coupled to said proximal ends of said control wire, said inner catheter, and said outer catheter for moving said inner catheter relative to said outer catheter such that said distal end of said inner catheter extends through said automatic sealing means, and for moving said control wire relative to said inner catheter such that said sampling brush extends past said distal end of said inner catheter.

5. A protected microbiological sampling brush assembly, comprising:
   a) a control wire having a proximal end and a distal end;
   b) a sampling brush coupled to said distal end of said control wire;
   c) an inner catheter having a proximal end, a distal end, and a lumen extending from said proximal end to said distal end, said control wire being disposed within said lumen of said inner catheter;
   d) an outer catheter having a proximal end, a distal end, and a lumen extending from said proximal end to said distal end, said inner catheter being disposed within said lumen of said outer catheter;
   e) automatic sealing means coupled to said distal end of said outer catheter for sealing access to said lumen of said outer catheter, said automatic sealing means being automatically opened by distal movement of said inner catheter relative to said outer catheter and being automatically closed by proximal movement of said inner catheter relative to said outer catheter; and
   f) proximal actuation means for moving said inner catheter relative to said outer catheter such that said distal end of said inner catheter extends through said automatic sealing means, and for moving said control wire relative to said inner catheter such that said sampling brush extends past said distal end of said inner catheter, said proximal actuation means including a handle coupled to said proximal end of said outer catheter and a rotatable lever coupled to said handle, said lever progressively engaging said proximal end of said inner catheter and said proximal end of said control wire so that said inner catheter opens said automatic sealing means prior to said sampling brush extending past said inner catheter.

6. An assembly according to claim 5, wherein:
   when said inner catheter is in a retracted position, said inner catheter is moved distally relative to said outer catheter before said control wire is moved distally relative to said inner catheter.

7. An assembly according to claim 5, wherein:
   said proximal actuation means further includes a first rack member coupled to said proximal end of said inner catheter and a second rack member coupled to said proximal end of said control wire, said lever having a first pinion means for engaging said first rack member and second pinion means for engaging said second rack member.

8. An assembly according to claim 7, wherein:

said first rack member has a throughbore through which said control wire extends.

9. An assembly according to claim 7, wherein: said lever has a substantially arcuate surface from which said first pinion means and said second pinion means extend, said first and second rack members are substantially coaxial, said first rack member has a first groove of a first depth, said second rack member has a second groove of a second depth deeper than said first depth, and said first pinion means has a first height and second pinion means has a second height higher than said first height.

10. A protected microbiological sampling brush assembly, comprising:

a) a control wire having a proximal end and a distal end;

b) a sampling brush coupled to said distal end of said control wire;

c) an inner catheter having a proximal end, a distal end, and a lumen extending from said proximal end to said distal end, said control wire being disposed within said lumen of said inner catheter;

d) an outer catheter having a proximal end, a distal end, and a lumen extending from said proximal end to said distal end, said inner catheter being disposed within said lumen of said outer catheter;

e) automatic sealing means coupled to said distal end of said outer catheter for sealing access to said lumen of said outer catheter, said automatic sealing means being automatically opened by distal movement of said inner catheter relative to said outer catheter and being automatically closed by proximal movement of said inner catheter relative to said outer catheter; and f) proximal actuation means for moving said inner catheter relative to said outer catheter such that said distal end of said inner catheter extends through said automatic sealing means, and for moving said control wire relative to said inner catheter such that said sampling brush extends past said distal end of said inner catheter, said proximal actuation means including a handle coupled to said proximal end of said outer catheter and a rotatable lever coupled to said handle, said lever progressively engaging said proximal end of said inner catheter and said proximal end of said control wire so that when said inner catheter is extending past and through said automatic sealing means and said sampling brush is extending past said inner catheter, said sampling brush is pulled back into said inner catheter prior to said inner catheter being completely pulled back into said automatic sealing means such that said automatic sealing means closes.

11. An assembly according to claim 10, wherein:

when said inner catheter is in an extended position, said control wire is moved proximally relative to said inner catheter before said inner catheter is moved proximally relative to said outer catheter.

12. A protected microbiological sampling brush assembly, comprising:

a) a control wire having a proximal end and a distal end;

b) a sampling brush coupled to said distal end of said control wire;

c) an inner catheter having a proximal end, a distal end, and a lumen extending from said proximal end to said distal end, said control wire being disposed within said lumen of said inner catheter;

d) an outer catheter having a proximal end, a distal end, and a lumen extending from said proximal end to said distal end, said inner catheter being disposed within said lumen of said outer catheter;

e) automatic sealing means coupled to said distal end of said outer catheter for sealing access to said lumen of said outer catheter, said automatic sealing means being automatically opened by distal movement of said inner catheter relative to said outer catheter and being automatically closed by proximal movement of said inner catheter relative to said outer catheter; and f) proximal actuation means for moving said inner catheter relative to said outer catheter such that said distal end of said inner catheter extends through said automatic sealing means, and for moving said control wire relative to said inner catheter such that said sampling brush extends past said distal end of said inner catheter, said proximal actuation means including a handle coupled to said proximal end of said outer catheter, a first rack member coupled to said proximal end of said inner catheter, a second rack member coupled to said proximal end of said control wire, a first pinion means for engaging said first rack member, a second pinion means for engaging said second rack member, and a trigger actuated third rack member progressively engaging said first and second pinion means so that said inner catheter opens said automatic sealing means prior to said sampling brush extending past said inner catheter.

13. An assembly according to claim 12, wherein:

when said inner catheter is in a retracted position, said inner catheter is moved distally relative to said outer catheter before said control wire is moved distally relative to said inner catheter.

14. An assembly according to claim 12, wherein:

said first rack member has a throughbore through which said control wire extends.

15. An assembly according to claim 12, wherein:

said trigger actuated third rack member is spring biased.

16. An assembly according to claim 12, wherein:

when said inner catheter is in a retracted position, said inner catheter is moved distally relative to said outer catheter before said control wire is moved distally relative to said inner catheter.

17. An assembly according to claim 12, wherein:

said first pinion means and said second pinion means each have a central axis substantially perpendicular to a longitudinal axis of said control wire, and said first pinion means and said second pinion means rotate about their respective central axes.

18. A protected microbiological sampling brush assembly, comprising:

a) a control wire having a proximal end and a distal end;

b) a sampling brush coupled to said distal end of said control wire;

c) an inner catheter having a proximal end, a distal end, and a lumen extending from said proximal end to said distal end, said control wire being disposed within said lumen of said inner catheter;

d) an outer catheter having a proximal end, a distal end, and a lumen extending from said proximal end to said distal end, said inner catheter being disposed within said lumen of said outer catheter;

e) automatic sealing means coupled to said distal end of said outer catheter for sealing access to said lumen of said outer catheter, said automatic sealing means being automatically opened by distal movement of said inner catheter relative to said outer catheter and being automatically closed by proximal movement of said inner catheter relative to said outer catheter; and f) proximal actuation means for moving said inner catheter relative to said outer catheter such that said distal end of said inner catheter extends through said automatic sealing means, and for moving said control wire relative to said inner catheter such that said sampling brush extends past said distal end of said inner catheter, said proximal actuation means including a handle coupled to said proximal end of said outer catheter, a first rack member coupled to said proximal end of said inner catheter, a second rack member coupled to said proximal end of said control wire, a first pinion means for engaging said first rack member, a second pinion means for engaging said second rack member, and a trigger actuated third rack member progressively engaging said first and second pinion means so that when said inner catheter is extending past and through said automatic sealing means and said sampling brush is extending past said inner catheter, said sampling brush is pulled back into said inner catheter prior to said inner catheter being completely pulled back into said automatic sealing means such that said automatic sealing means closes.

\* \* \* \* \*